United States Patent
Cheng et al.

(10) Patent No.: US 10,596,095 B2
(45) Date of Patent: Mar. 24, 2020

(54) METHOD FOR MOISTURIZING SKIN USING P-113 PEPTIDE

(71) Applicant: PACGEN LIFE SCIENCE CORPORATION, Vancouver (CA)

(72) Inventors: Wen-Chi Cheng, Hsinchu County (TW); Ming-Sun Liu, Hsinchu County (TW); Frank Lin, Hsinchu County (TW)

(73) Assignee: PACGEN LIFE SCIENCE CORPORATION, Vancouver (CA)

( * ) Notice: Subject to any disclaimer, the term of this patent is extended or adjusted under 35 U.S.C. 154(b) by 63 days.

(21) Appl. No.: 15/550,030

(22) PCT Filed: Feb. 4, 2016

(86) PCT No.: PCT/CN2016/073434
§ 371 (c)(1),
(2) Date: Aug. 10, 2017

(87) PCT Pub. No.: WO2016/127902
PCT Pub. Date: Aug. 18, 2016

(65) Prior Publication Data
US 2018/0028426 A1    Feb. 1, 2018

(30) Foreign Application Priority Data

Feb. 13, 2015  (CN) .......................... 2015 1 0080933

(51) Int. Cl.
*A61K 8/64* (2006.01)
*A61Q 19/00* (2006.01)
*A61K 8/02* (2006.01)
*A61Q 19/08* (2006.01)

(52) U.S. Cl.
CPC .............. *A61K 8/64* (2013.01); *A61K 8/0212* (2013.01); *A61Q 19/00* (2013.01); *A61Q 19/007* (2013.01); *A61Q 19/08* (2013.01); *A61K 2800/782* (2013.01)

(58) Field of Classification Search
CPC ........................................................ A61K 8/64
See application file for complete search history.

(56) References Cited

U.S. PATENT DOCUMENTS

| | | | | |
|---|---|---|---|---|
| 5,885,965 | A * | 3/1999 | Oppenheim | C07K 14/4723 514/1.1 |
| 2010/0316643 | A1* | 12/2010 | Eckert | A01N 37/46 424/134.1 |
| 2011/0039761 | A1* | 2/2011 | Eckert | A61K 8/64 514/2.4 |
| 2011/0039762 | A1* | 2/2011 | Eckert | A61K 8/64 514/2.4 |
| 2011/0039763 | A1* | 2/2011 | Eckert | A61K 8/64 514/2.4 |
| 2014/0065119 | A1* | 3/2014 | Lajoie | A61K 38/12 424/93.72 |
| 2014/0142028 | A1* | 5/2014 | Eckert | A01N 37/46 514/2.6 |
| 2014/0349917 | A1* | 11/2014 | Eckert | A61K 8/64 514/2.3 |

\* cited by examiner

*Primary Examiner* — Amber D Steele
(74) *Attorney, Agent, or Firm* — Hannah Tien

(57) ABSTRACT

A method for moisturizing skin using P-113 peptide, which comprises administering to the skin of a subject a composition containing a P-113 peptide, wherein the P-113 peptide comprises the sequence of SEQ ID NO: 1. P-113 peptide is hypoallergenic and non-cytotoxic, which means it does not cause harms or allergies to the skin and can be used as an ingredient of cosmetic products. The P-113 peptide fragment has moisture absorption and moisture retention effects, therefore it can be formulated with other ingredients of moisturizing cosmetic products, enhancing the moisturizing effect of other moisturizing ingredients. In addition, the P-113 peptide fragment is capable of inhibiting the production of MMP-9 and thus decreases collagen degradation, thereby achieving the anti-wrinkle and anti-aging effects. The cosmetic disclosed herein comprises not only the peptide, but also active ingredients of cosmetic products and essence liquid formulations.

2 Claims, 6 Drawing Sheets

Specification includes a Sequence Listing.

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens
<220> FEATURE:
<221> NAME/KEY: PEPTIDE

<400> SEQUENCE: 1

Ala Lys Arg His His Gly Tyr Lys Arg Lys Phe His
1               5                   10
```

METHOD FOR MOISTURIZING SKIN USING P-113 PEPTIDE

CROSS-REFERENCES TO RELATED APPLICATIONS

The present application is a 371 national stage application of PCT/CN2016/073434, filed on Feb. 4, 2016 and which, in turn, relies in China Application No. 201510080933.0, filed on Feb. 13, 2015, for priority. Each of the aforementioned applications is hereby incorporated by reference in its entirety.

The present application contains a Sequence Listing in computer readable form, which is incorporated herein by reference it its entirety.

FIELD OF THE INVENTION

The present invention relates to a use of a composition in preparing a cosmetic having a moisturizing effect, and more particularly to the use of a histatin peptide in preparing a moisturizing cosmetic.

BACKGROUND OF THE INVENTION

Cosmetics (or so called makeup), in addition to simple cleansing products, are currently considered as substances used to enhance person appearance. The main purpose of the cosmetics is to be topically applied to the skin to provide anti-aging, hydration and/or skin activation effects.

When getting old, or due to physiological or environmental factors, human skin develops conditions such as aging, skin roughening, or wrinkling. The skin of a normal young person maintains a certain degree of elasticity and tension. When facial muscles relax the skin reverses to its original condition and wrinkles disappear. However, upon reaching middle age, the skin begins to age and becomes thin, hard, dry, reduces its tension; dermal elastic fibers degenerate and fracture so as to result in reduced tension and reduced elasticity. Therefore, when the facial muscles relax, the skin does not reverse quickly to its original condition and wrinkles will be gradually formed. Moreover, as age progresses the skin and subcutaneous tissues are less firm, when coupled with facial support tissue atrophy or loss and slack muscles, deeper wrinkles will be formed due to the effect of gravity on the skin. Roughened skin is a skin problem resulted from dryness, ultraviolet, irritating substances such as cleansing agents or chemical substances and other important extrinsic factors, or impaired hormonal balance and other important intrinsic factors. It is accompanied by compromised barrier function of the stratum corneum, reduced moisture content in the stratum corneum, hypermetabolic turnover of the epidermis, generation of psoriasis scales resulting in roughened stratum corneum. So, when cells on the skin lose elasticity and moisturizing function, the skin folds, dries and loses radiance.

"Peptide" is a skin care ingredient that attracts considerable interests. It is a small molecule substance composed of amino acids. Since amino acid is the smallest unit of a protein, the volume of a peptide is much smaller than that of an average protein. Peptides are easy to be absorbed by cells in the body and can stimulate human body to generate rapid responses. A peptide is much easier to be absorbed by the skin as compared to collagen, elastin or other macromolecular proteins. As natural ingredients, peptides are less irritating to human body and can be used as skin care products having anti-aging, wrinkle-removing, anti-inflammatory, skin tolerance-strengthening, melanin reducing effects to activate and regenerate tender, elastic and shiny skin. A peptide can be composed of two to several tens of amino acids, for example, a dipeptide is composed of two amino acids, a tripeptide is composed of three amino acids. Polypeptides having small molecular amino acid can penetrate the epidermal layer and reach the basal layer to repair damaged cells with their biological activities.

Therefore, in the era of global aging and high demand for skin care, it is an important issue how to develop a novel ingredient for skin care solution in order to provide water retaining and moisturizing effect.

SUMMARY OF THE INVENTION

The present invention provides a method for moisturizing skin using P-113 peptide, which comprises administering to the skin of a subject a composition containing a P-113 peptide, wherein the P-113 peptide comprises the sequence of SEQ ID NO: 1. P-113 peptide is hypoallergenic and non-cytotoxic, which means it does not cause harms or allergies to the skin and can be used as an ingredient of cosmetic products. The P-113 peptide fragment has moisture absorption and moisture retention effects, therefore it can be formulated with other ingredients of moisturizing cosmetic products, enhancing the moisturizing effect of other moisturizing ingredients. In addition, the P-113 peptide fragment is capable of inhibiting the production of MMP-9 and thus decreases collagen degradation, thereby achieving the anti-wrinkle and anti-aging effects. The cosmetic of the present invention comprises not only the peptide, but also active ingredients of cosmetic products and essence liquid formulations. Accordingly, it not only provides major effects such as moisturizing and anti-wrinkle, but also enhances other composite functions, such as astringent effect, whitening, anti-aging, anti-oxidation or skin tissue activation.

DETAILED DESCRIPTION OF THE INVENTION

Figure 1:
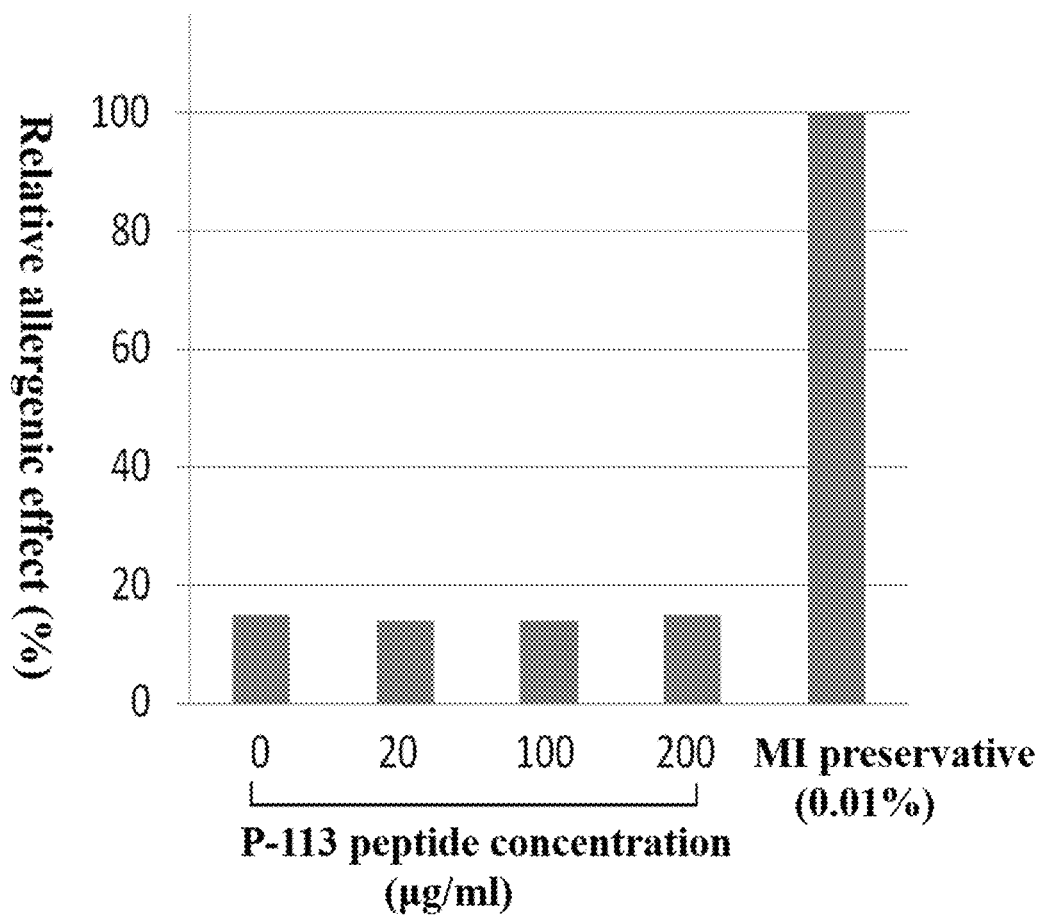
FIG. 1 shows the comparative analysis of the allergenic effect caused by P-113 and the MI preservative.

The present invention discloses a novel cosmetic ingredient comprising a histatin peptide and a cosmetic active ingredient as the main ingredients and an application thereof. The histatin peptide of the present invention has moisturizing and anti-wrinkle effect. It has been found that after the histatin peptide and hyaluronic acid as well as a variety of other plant extracts and other cosmetic active ingredients are formulated, it provides a synergistic effect as well as moisturizing, anti-aging, skin tissue activation and other effects, and further, the peptide is non-allergenic to skin.

The scope of the present invention should not be limited by any of the described exemplary embodiments. More precisely, these embodiments are provided by way of illustration only and so that this disclosure will be thorough, complete and will fully convey the full scope of the invention to those skilled in the art. In the instant specification, descriptions and details of well-known features and techniques may be omitted to avoid unnecessarily obscuring the described embodiments of the present invention.

The terminology used in the description is merely for the purpose of describing the particular versions and embodiments, and is not intended to limit the scope of the present invention. The terms "comprises" and/or "comprising" or "includes" and/or "including" when used in the instant specification, specify the presence of stated features, regions, integers, steps, operations, elements, components, and/or groups thereof, however, the presence or addition of one or more other features, regions, integers, steps, operations, elements, components, and/or groups thereof are not excluded. Unless otherwise indicated, all terms (including technical and scientific terms) used herein are the same as those commonly understood by one of ordinary skill in the art. It will be further understood that, for example, the terminology commonly used in the dictionary should be construed so as to be consistent with the related art and the context of the invention; unless otherwise defined, it will not be idealized or exceeded its formal meaning.

As used herein, the terms "a," "one" and "the" refers "one or more," the terms are intended for convenience only and to give the basic idea of the present invention. This description is to be understood as including one or at least one, and includes plural numbers unless expressly otherwise indicated.

As used herein, the term "or" is intended to mean "and/or."

The present invention provides a use of a composition in preparing a cosmetic having a moisturizing function, wherein the composition comprises a P-113 peptide, wherein the P-113 peptide has the sequence of SEQ ID NO: 1.

In one embodiment, the cosmetic is a cosmeceutical product.

In another embodiment, the P-113 peptide is selected from a histatin-5. In a preferred embodiment, the P-113 peptide is composed of 24 amino acids from a histatin-5. In a more preferred embodiment, the P-113 peptide is a 12-functional amino acid fragment of the 24 amino acids from the histatin-5. Thus, the P-113 peptide is a dodecapeptide, and the amino acid sequence of the P-113 peptide is SEQ ID NO: 1, its amino acid sequence is AKRHH-GYKRKFH, its chemical formula is as follows:

The P-113 peptide can be prepared or obtained in accordance to U.S. Pat. Nos. 5,631,228, 5,646,119, 5,885,965 and 5,912,230. These patents disclose the amino acid sequence of the histatin family and the amino acid sequence of the P-113 peptide.

In one embodiment, the P-113 peptide is a modified P-113 peptide fragment. In a preferred embodiment, the modification comprises repeating the sequence of the P-113 peptide, protein processing, glycosylation, carboxy terminal amidation or amino acid isomerization.

In another embodiment, the moisture absorption rate of the P-113 peptide fragment is from 30% to 80%/o. In a preferred embodiment, the moisture absorption rate of the P-113 peptide fragment is from 40% to 70/a %.

In one embodiment, the moisture retention rate of the P-113 peptide is from 70% to 100%. In a preferred embodiment, the moisture retention rate of the P-113 peptide is from 80% to 90%.

In one embodiment, the P-113 peptide is hypoallergenic and non-cytotoxic.

In another embodiment, the P-113 peptide has an anti-wrinkle function that decreases the degradation of collagen on the skin by inhibiting the matrix metallopotinase-9 (MMP-9). Therefore, by decreasing collagen degradation on the skin, that is, inhibiting the production of MMP-9, the P-113 peptide prevents the skin from wrinkling and aging.

The cosmetic described herein, i.e. the cosmetic products which comprise the aforementioned P-113 peptide, include but are not limited to masks, facial cleansers, exfoliating gels, toning lotions, essence liquids, lotions, creams or sunscreen lotions, etc. In one embodiment, the cosmetic dosage form is a mask, a facial cleanser, an exfoliating gel, an essence liquid, a toning lotion, a lotion, a cream or a sunscreen. In a preferred embodiment, the cosmetic is selected from the group consisting of a humectant, an ointment, a cleanser, a makeup remover, a toning lotion, a night care agent, a skin repair agent, a sunscreen agent, a skin whitening agent, a colored foundation, eye shadow and suntan agent (tanner). Therefore, the P-113 can be formulated as a cosmetic composition, such as a skin-softening lotion, an astringent toning lotion, a moisturizing lotion, a nourishing essence, a nourishing cream, a massage cream, an essence, an eye cream, an eye essence, a cleansing cream, a cleansing foam, a cleansing water, a cosmetic kit, a gel, a make-up powder, a foundation, a body lotion, a body cream, a massage oil, a body essence, or similar compositions. In addition, it can be formulated as a transdermal formula, such as a toning lotion, an ointment, a gel, a lotion, a patch or a

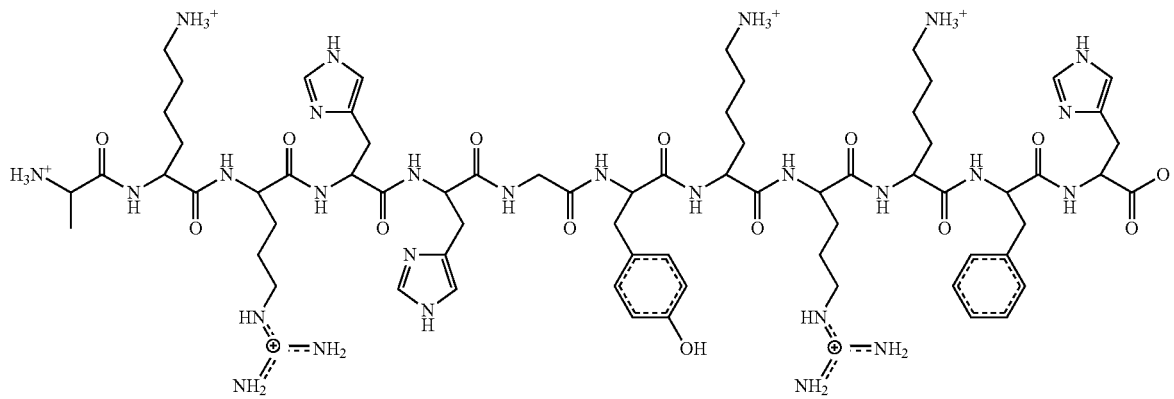

spray. According to one embodiment, the cosmetic composition can be used to moisturize the skin.

In one embodiment, the cosmetic further comprises other effective skin care ingredients. In a preferred embodiment, the cosmetic further comprises an essence liquid formulation, wherein the essence liquid formulation comprises a natural moisturizing factor, a humectant, a low carbon alcohol, an emulsifier, an emollient, a polymeric gel, a plant extract or active ingredients. In a more preferred embodiment, the essence liquid formulation further comprises an auxiliary ingredient, wherein the auxiliary ingredient comprises an antibacterial agent, a preservative, a chelating agent, an acid-base adjusting agent or a fragrance.

The term "natural moisturizing factor" as used herein includes, but is not limited to, hyaluronic acid, PCA-NA, and the like. The term "humectant" includes, but is not limited to, Glycerin, 1,3-butylene glycol, propylene glycol, Sorbitol, and the like. The term "lower carbon alcohol" includes, but is not limited to, ethanol, isopropyl alcohol, and the like. The term "emulsifier" includes, but is not limited to, PEG-40 hydrogenated castor oil, Xanthum Gum, and the like. The term "emollient" includes, but is not limited to, refined natural oils, ethoxylated esters. The term "polymeric gel" includes, but is not limited to, hydrolyzed collagen, gum arabic, hydroxyethyl cellulose (HEC), polyacrylic acid (Carbopol 940), and the like. The term "active ingredients" include but are not limited to allantoin, vitamin B5 (panthenol), coenzyme Q10, and the like.

The P-113 peptide-containing cosmetic provided by the present invention has the following advantages when compared with other prior arts:

(1) The peptide-containing skin moisturizing product of the present invention is a product that contains the P-113 peptide fragment which is an active peptide composed of 12 amino acids on a histatin, which is hypoallergenic and non-cytotoxic, that is, it does not cause harms and allergies to the skin and can be used as an ingredient of the cosmetic.

(2) The P-113 peptide fragment has the moisturizing and water retention effect, when formulated with other cosmetic moisturizing ingredients, the moisturizing effect of other moisturizing ingredients are enhanced. In addition, the P-113 peptide fragment can inhibit the production of MMP-9, collagen degradation is thus reduced, thereby providing anti-wrinkle and anti-aging effect.

(3) The cosmetic provided by the present invention comprises, in addition to the peptide, cosmetic active ingredients and essence liquid formulations, which enhance, in addition to moisturizing and anti-wrinkle effect, other composite functions such as astringent, whitening, anti-aging, anti-oxidation or skin tissue activation effect.

EXAMPLES

The present invention may be embodied in different forms, and is not limited to the examples mentioned below. The following examples are merely representative of various aspects and features of the present invention.

(1) P-113 Peptide Preparation

The P-113 peptide of the present invention is an amino acid fragment of human salivary histatine-5, which is composed of 12 amino acids from histatine-5, and the sequence thereof is SEQ ID NO: 1, the chemical formula is as follows:

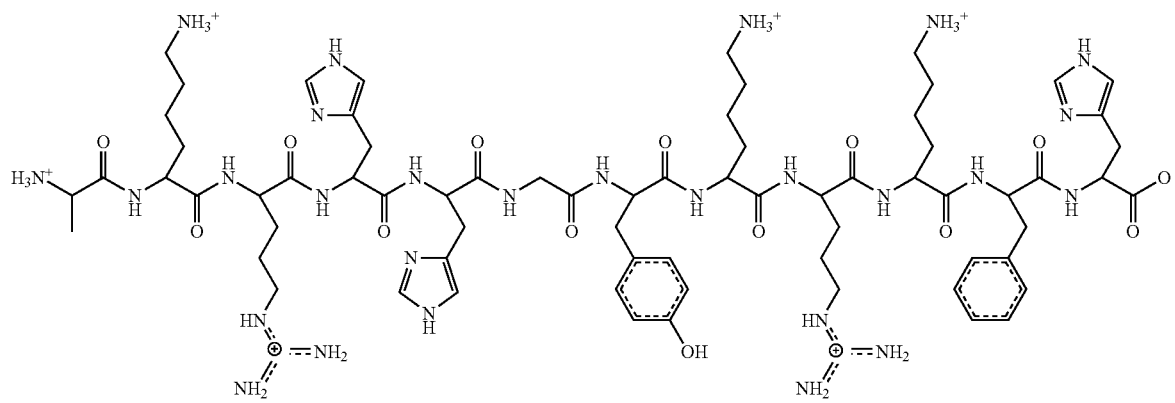

The amino acid sequence of P-113 peptide was synthesized and prepared according to the procedure disclosed in four U.S. Pat. Nos. 5,631,228, 5,646,119, 5,885,965 and 5,912,230.

(2) Allergenicity and Cytotoxicity Assessment of P-113 Peptide

The present invention studied the problem of allergenicity and cytotoxicity of P-113 peptide by allergenicity and cell survival assays. The principle for assessing the hypoallergenic characteristic of P-113 was to use degranulation as the indicator of the involvement of basophils with inflammatory responses. When allergic reaction occurred, allergens bound with the receptors on basophils, releasing mediators of the physiological effects, such as histamine, heparin, β-hexosaminidase, etc.

In the present invention, Rat basophilic leukemia cell line (RBL-2H3) was used to treat P-113 peptide and Methylisothiazolinone (MI), a preservative often added conventionally to cosmetics, a spectrophotometer was used for detection at a wavelength of 405 nm to analyze the release of allergenic mediators and to assess the allergenicity of the cosmetic raw material.

When the cosmetic raw material caused allergies in cells, histamine and β-hexosaminidase were released in large quantities. In the present invention, from low to high concentration (0, 20, 100 and 200 μg/ml) of P-113 peptide and the MI preservative (the concentration was about 0.01%)

were used to treat the RBL-2H3 cell line, the β-hexosaminidase release rate after degranulation was detected, which was used as the basis of the allergenic results.

As shown in FIG. 1, the results of the allergenicity assessment showed that when treated with from low to high concentration of P-113 peptide, no allergic reaction was observed, and when compared with the MI preservative, the level of allergenicity was extremely low. Only sporadic cases showed that the currently used MI preservative was skin-irritating and causing allergic reactions, the allergenicity level of P-113 was relatively low, Therefore, it was obvious that P-113 when used in cosmetics is quite safe.

The cytotoxicity test was performed with Methylthiazol tetrazolium bromide (MTT) assay to test the cell survival rate. The principle was that MTT is a water-soluble yellow dye, after reacting with cells it was reduced by the NADPH in the cells to become an insoluble dark blue crystal, then the blue crystal was dissolved with dimethyl sulfoxide (DMSO), the absorbance value was analyzed, the stronger the cell activity, the darker the blue, and when the cell was dead, it became yellow.

In the present invention, from low to high concentration (0, 20, 100 and 200 μg/ml) of P-113 peptide and the MI preservative were used to treat the cells for 2 hours, then the MTT solution was added for reaction, a spectrophotometer at the wavelength of 595 nm was used to analyze the cell survival rate, and the harmful toxic effect of the cosmetic raw material on the cells was determined.

Figure 2:
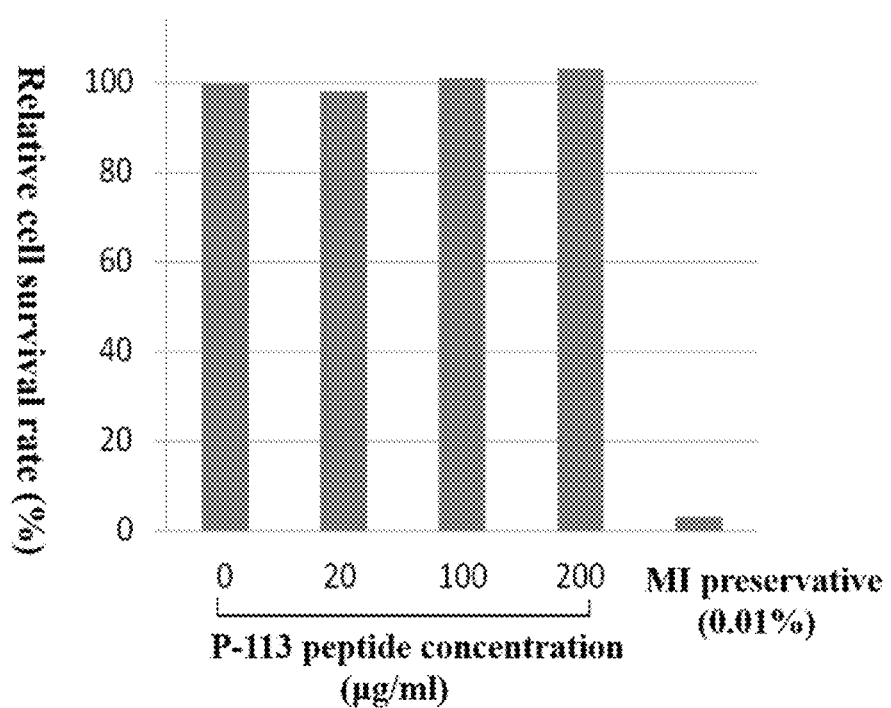
FIG. 2 is the comparative analysis of the cell survival rate of the P-113 peptide and the MI preservative.

As shown in FIG. 2, in the analysis of the cell survival rate, after being treated with different concentrations of P-113 peptide, it was found that the cells were not affected and still maintained good activities, but the MI preservative decreased the cell survival rate. The result of the MTT assay showed that the P-113 peptide was a good cosmic raw material with no cytotoxicity. Therefore, based on the above results the P-113 peptide was a non-allergenic and non-cytotoxic ingredient.

(3) Determination of Moisture Absorption and Moisture Retention of P-113 Peptide The moisture absorption of the P-113 peptide was determined by dissolving magnesium chloride ($MgCl_2$) and potassium chloride (KCl), two types of salts, in water, preparing supersaturated solutions based on the respective solubility of these two types of salts, placing the solutions in sealed bottles to create a relative humidity of 32% and 84%, respectively, then taking P-113 peptide and hyaluronic acid for comparison test. The hyaluronic molecule of hyaluronic acid could carry up to 500 folds of water. The hyaluronic acid is currently recognized as the best moisturizing ingredient, and widely used in cosmetics and skincare products.

0.1 g of P-113 peptide and hyaluronic acid powder were weighed and placed in the internal chamber of a Conway's dish, saturated solutions were added in the external chamber, oil was applied on the rim of the Conway's dish lid to seal it completely, placed in an oven at 30° C. for 24 hours, then samples were removed and weighed.

Moisture absorption rate under different humidity was calculated by the following formula:

$$\text{Moisture absorption rate } (\%) = [(Wt-W0)/W0] \times 100\%$$

wherein W0: the weight (g) of the initial sample, and Wt: the weight (g) of the sample removed after 24 hours.

Figure 3:
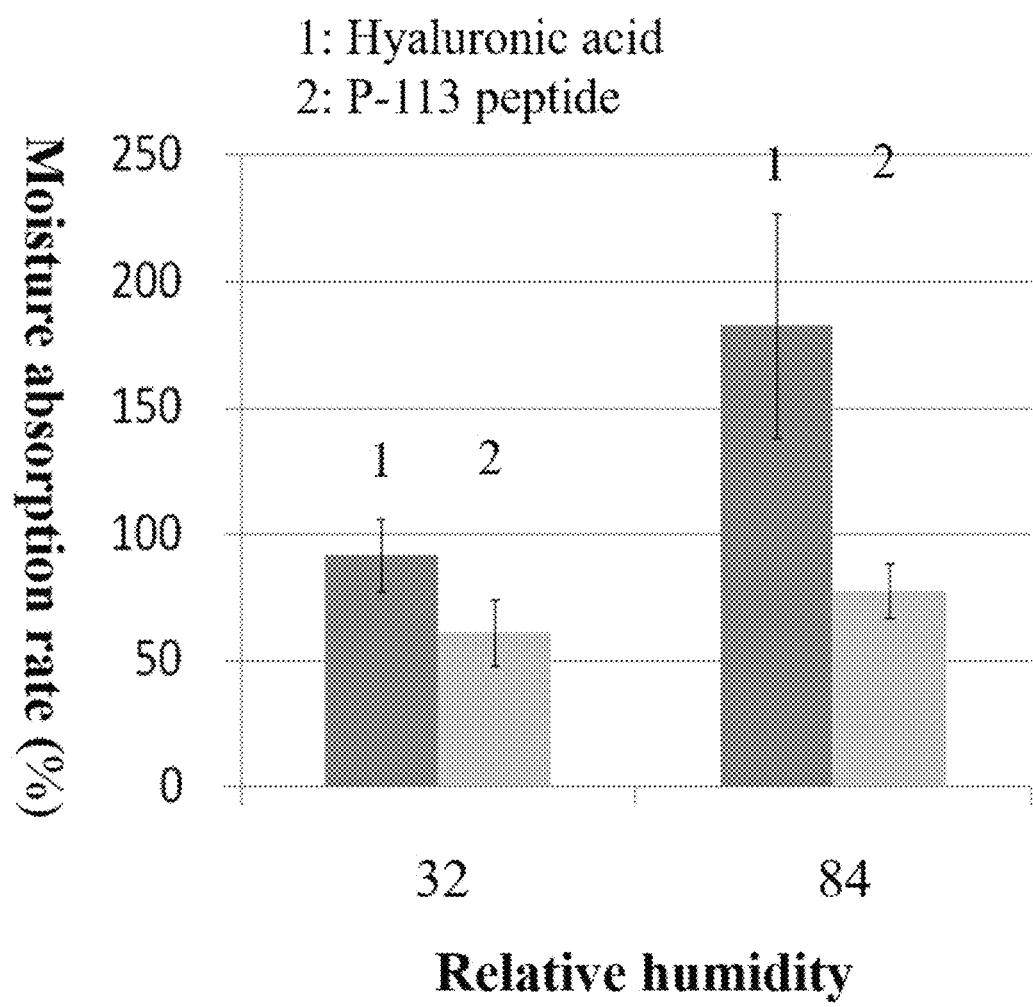
FIG. 3 shows the experimental results of the moisture absorption rate of the P-113 peptide.

As shown in FIG. 3, the moisture absorption rate of the hyaluronic acid at the relative humidity of 32% in the first experiment was 100%, and the moisture absorption rate of the P-113 peptide and the hyaluronic acid at the relative humidity of 32% and 84% were compared. The moisture absorption rate of the P-113 peptide at the relative humidity of 32% was 70% of that of the hyaluronic acid, and the moisture absorption rate was 40% even at the high relative humidity (84%).

In addition, the moisture retention and water absorption of P-113 peptide were determined by dissolving magnesium chloride ($MgCl_2$) and potassium chloride (KCl), two types of salts, in water, preparing supersaturated solutions based on the solubility of these two types of salt respectively, separately placing in sealed bottles to create a relative humidity of 32% and 84% respectively, then using P-113 peptide and hyaluronic acid for comparison test.

0.1 g of P-113 peptide and hyaluronic acid powder were weighed and placed in the internal chamber of a Conway's dish, then 0.1 ml of deionized water was added, saturated solutions were then added in the external chamber, sealed with the Conway's dish lid and placed in the oven at 30° C. for 24 hours, then samples were removed and weighed.

Moisture retention at different humidity levels was calculated according to the following formula:

$$\text{Moisture retention rate } (\%) = [1-((Wt-W0)/W0)] \times 100\%$$

wherein W0: the weight (g) of the initial sample, and Wt: the weight (g) of the sample removed after 24 hours.

Figure 4:
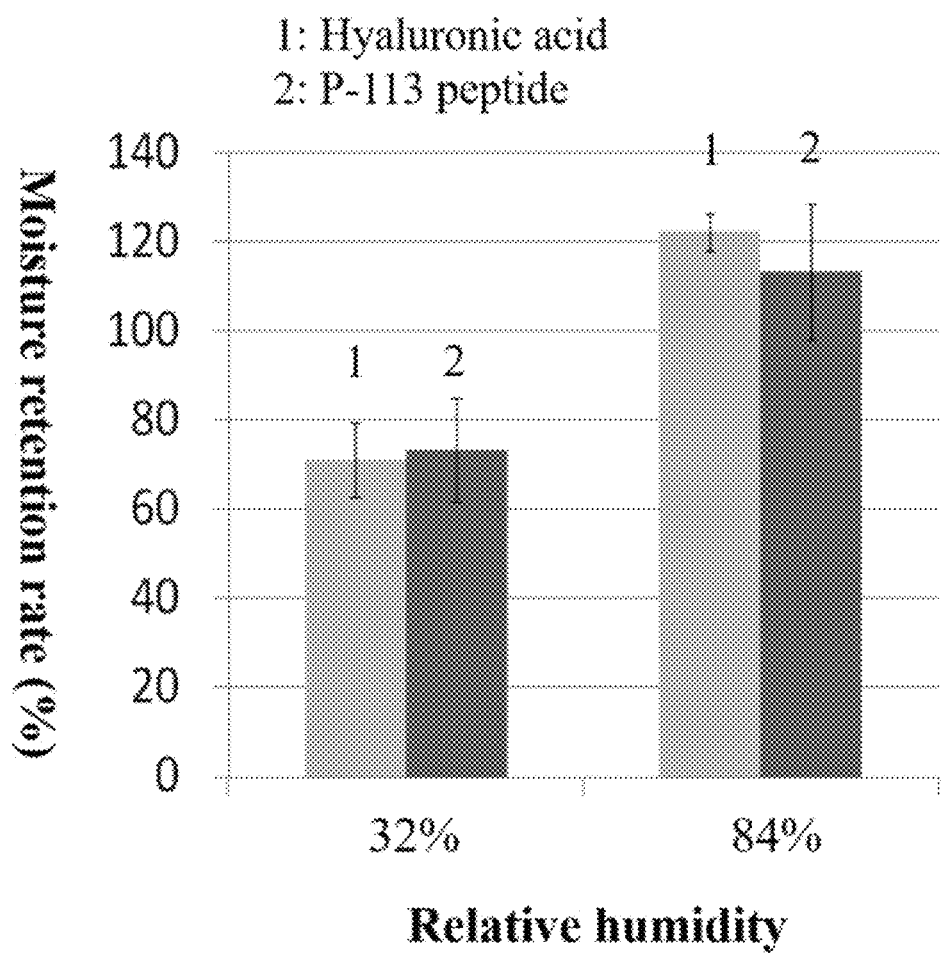
FIG. 4 shows the experimental results of the moisture retention rate of the P-113 peptide.

As shown in FIG. 4, the moisture retention rate of the hyaluronic acid at a relative humidity of 32% in the first experiment was 100%, then the moisture retention rate of the P-113 peptide and hyaluronic acid at a relative humidity of 32% and 84% were compared. The moisture retention rate of the P-113 peptide, as compared to the hyaluronic acid, was no worse than that of the hyaluronic acid at the relative humidity of either 32% or 84%, which indicated that the P-113 peptide had excellent moisture retention. The above results showed that the moisture absorption rate of the P-113 peptide could reach from 40% to 70%, and the moisture retention rate could reach 100%, similar to the effect of the hyaluronic acid.

(4) Evaluation of Anti-Wrinkle and Anti-Aging Effect of P-113 Peptide

Collagen is the main structural protein of the body, composed of three protein chains that coiled together in a tight triple helices to form fibrils. The fibrils are cross-linked in the extracellular matrix to provide the structural frame surrounding the cells, which is helpful in supporting cell formation and differentiation. The mesh-like collagen network enables the cells to be bound together, and provides the supportive framework and environment for the cells to develop and function. The stimulation of collagen provides strength, durability, smoothness, richness to the appearance of the skin.

MMP-9 in matrix metalloproteinases is a type IV collagenase, gelatinase or gelatinase B (GELB), and its molecular weight is 92 kDa. MMP-9 degrades the extracellular matrix of the connective tissue, such as proteoglycan, fibronectin, laminin, elastin, and collagen, and inhibits the synthesis of procollagen. The degradation of these macromolecules results in wrinkling and aging of the skin.

Therefore, the anti-wrinkle effect of the P-113 peptide was evaluated in the present invention by enzyme activity inhibition test of the Matrix metallopoateinase-9 (MMP-9). The matrix metallopoateinase was a part of the secreted and membrane-bound zinc endopeptidases, capable of degrading the extracellular matrix (ECM).

Figure 5:
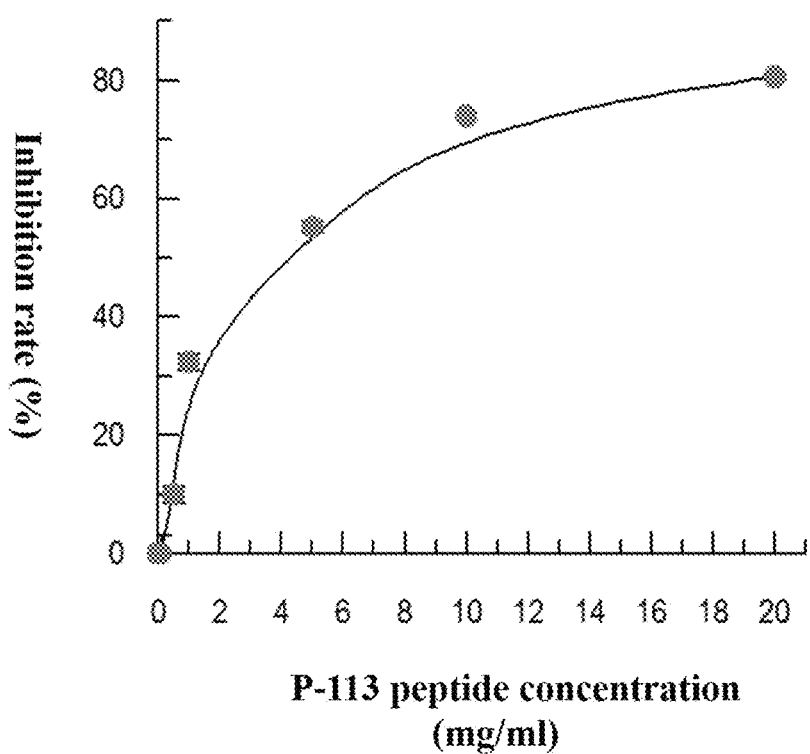
FIG. 5 shows the inhibitory effect of the P-113 peptide on MMP-9.

The enzyme activity inhibition test of the MMP-9 was conducted to evaluate the anti-wrinkle effect of the P-113 peptide. In the present invention the ability of P-113 peptide to inhibit MMP-9 was tested by a SensoLyte® 520 MMP-9 Assay Kit. As shown in FIG. 5, the inhibition rate of the MMP-9 by the P-113 peptide was $IC_{50}=3.50\pm3.89$ mg/mL (see table 1 for detail data). The results showed that the P-113 peptide had the inhibitory activity against MMP-9, which meant that the P-113 peptide was able to protect collagen, elastin and other macromolecules from being degraded, thereby achieving the effect of anti-wrinkle and anti-aging.

TABLE 1

| Inhibition rate of MMP-9 proteinase | | |
| --- | --- | --- |
| P-113 concentration (mg/mL) | MMP-9 inhibition rate (%) | Standard error (SE) |
| 20 | 80.52 | 0.32 |
| 10 | 73.86 | 0.59 |
| 5 | 55.11 | 1.03 |

TABLE 1-continued

| Inhibition rate of MMP-9 proteinase | | |
| --- | --- | --- |
| P-113 concentration (mg/mL) | MMP-9 inhibition rate (%) | Standard error (SE) |
| 1 | 32.27 | 1.50 |
| 0.5 | 9.85 | 1.36 |
| 0 | 0 | 0 |

(5) Application of P-13 Peptide to Masks

From the above experiments, it was obvious that the P113-peptide had antibacterial, moisturizing, hypoallergenic and anti-wrinkle, skin care effects, therefore, in the present invention the P-113 peptide was applied to producing a mask.

Figure 6:
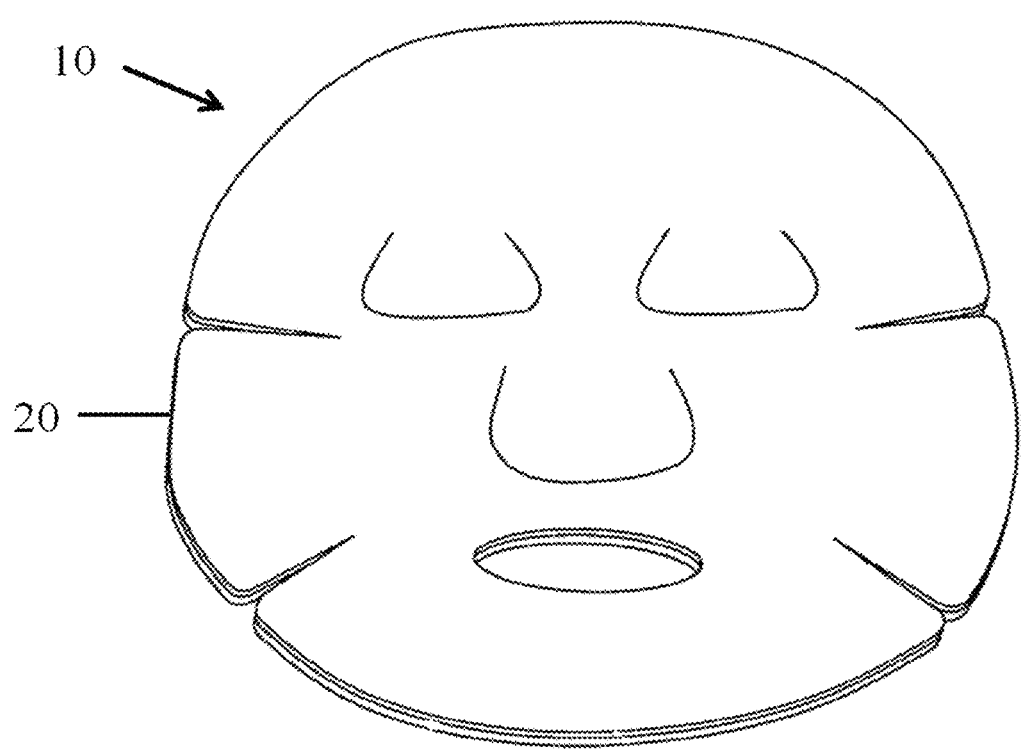
FIG. 6 is a diagram showing the appearance of a peptide-containing mask of the present invention.

As shown in FIG. 6, a peptide-containing mask 10 of the present invention comprised a mask body 20, wherein the mask body 20 was in a shape corresponding to a person's face, and further comprised a plurality of openings corresponding to two eyes, one nose and one mouth.

The mask body 20 comprised a plurality of skin care essences, wherein a primary skin care essence was a dodecapeptide composed of 12 amino acids, wherein the dodecapeptide was a P-113 peptide derived from human salivary histatin-5 fragment. In addition, the primary skin care essence of the mask body 20 further comprised a cosmetic active ingredient. The mask body 20, in addition to the primary skin care essence, further comprised an essence liquid formulation and an auxiliary ingredient to further provide a composite function, for example, supplying water, nutrients, and natural moisturizers necessary to the skin, achieving true skin activation and regeneration, and providing tender, elastic, shiny, whitening and other cosmetic effects.

The above description is the specific description of one preferred embodiment of the present invention, which is not intended to be limiting. Accordingly, any variations and modifications of the invention made by one skilled in the art within the scope and spirit of the invention are all within the scope of the invention.

What is claimed is:

1. A method for improving personal appearance of a subject, comprising topically applying to the skin of the subject a cosmetic comprising a P-113 peptide, wherein the P-113 peptide comprises the sequence of SEQ ID NO: 1, wherein the topic application of the cosmetic moisturizes the skin and improves water retention of the skin.

2. The method of claim 1, wherein the cosmetic is a mask, a facial cleanser, an exfoliating gel, a toning lotion, a lotion, a cream or a sunscreen lotion.

* * * * *